US00PP23398P3

(12) United States Plant Patent
Cain

(10) Patent No.: US PP23,398 P3
(45) Date of Patent: Feb. 19, 2013

(54) GRAPEVINE 'IFG FIVE'

(50) Latin Name: *Vitus vinifera*
Varietal Denomination: IFG Five

(75) Inventor: David Cain, Bakersfield, CA (US)

(73) Assignee: International Fruit Genetics LLC, Bakersfield, CA (US)

( * ) Notice: Subject to any disclaimer, the term of this patent is extended or adjusted under 35 U.S.C. 154(b) by 0 days.

(21) Appl. No.: 13/134,948

(22) Filed: Jun. 22, 2011

(65) Prior Publication Data

US 2012/0331597 P1 Dec. 27, 2012

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

PP4,787 P 11/1981 Olmo et al.
PP17,875 P3 7/2007 Gargiulo

*Primary Examiner* — Annette Para

(57) ABSTRACT

This invention is a new and distinct grapevine variety named 'IFG Five' which is characterized by producing extremely large purple to black, firm, elongated oval seeded grapes borne on large clusters. The fruit ripen and are harvestable in mid-August.

1 Drawing Sheet

Latin name of the genus and species claimed: *Vitus vinifera.*

Variety denomination: 'IFG Five'.

BACKGROUND OF THE INVENTION

The new and distinct grapevine described and claimed herein originated from a hand pollinated cross of the (Redglobe variety U.S. Plant Pat. No. 4,787 expired) and the Summer Royal variety (non-patented) performed in May of 2001. The seeds were subsequently germinated and the resulting plants were planted in the field in April 2002. The present variety of grapevine was selected as a single plant in August of 2003 and was first asexually propagated by hardwood cuttings in December of 2003 near Delano, Kern County, Calif. The resulting propagules were planted during April 2004 near Delano, Kern County, Calif. and were found to reproduce true-to-type through at least two generations of asexual reproduction.

BRIEF SUMMARY OF THE INVENTION

The new grapevine 'IFG Five' is characterized by producing extremely large, elongated oval seeded purplish to black berries borne on large clusters. The vine is very productive with short spur pruning and the fruit ripen 7 to 10 days before its maternal parent variety Redglobe. Berries have firm texture and excellent eating quality. It attains full black color with difficulty and may exhibit green or red coloration around the pedicle under some conditions. Application of the growth regulator ethrel allows full coloration.

The new grape vine differs from its parent the Redglobe variety by ripening 7 to 10 days earlier and by having larger more elongated berries which are black in color as opposed to the rounder red berries of Redglobe. It differs from its pollen parent by producing much larger seeded berries as opposed to the smaller seedless berries of the Summer Royal variety. To the inventor's knowledge, the known variety to which the new grapevine variety is most similar is the 'Black Globe' (U.S. Plant Pat. No. 17,875 P3). 'IFG Five' can be distinguished from Black Globe by ripening earlier (mid to late August as opposed to early to mid September for Black Globe), by having a more elongated ovate shape as opposed to the obovoid shape of 'Black Globe'. 'IFG Five' is more productive than the 'Black Globe' variety and can be spur pruned and still be highly productive while the 'Black Globe' is only medium productive and requires more costly cane pruning to maximize bunch counts. Mature clusters of 'IFG Five' are somewhat larger than 'Black Globe' and the peduncle is longer.

BRIEF DESCRIPTION OF THE FIGURE

The accompanying photographic illustration in FIG. 1 illustrates in full color 'IFG Five'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Five' plants grown in the vicinity of Delano, Kern County, Calif. during 2009, and is believed to apply to plants of the variety grown under similar conditions of soil and climate elsewhere:

VINE

General:
- *Size*.—Large.
- *Vigor*.—Medium.
- *Density of foliage*.—Medium.
- *Productivity*.—Very productive. Root stock — Own root.
- *Training method*.—Typically spur pruned leaving 2 bud spurs.

Trunk:
- *Trunk diameter of* 4-year-old vines at 30 cm above the soil line.—6.2 cm.
- *Shape*.—Stocky.
- *Straps*.—Very long — Continuous.
- *Surface texture*.—Medium.
- *Inner bark color*.—Can be any of the following colors; Greyed-orange 165A, and 166A, and 177B and 177C.

SHOOTS

Young shoot:
- *Form of tip*.—Wide open.
- *Distribution of anthocyanin coloration of tip*.—Absent.
- *Intensity of anthocyanin coloration of tip*.—Absent.
- *Density of prostrate hairs of tip*.—Sparse.
- *Density of erect hairs of tip*.—Absent.
- *Color*.—144A.

Woody shoot (Mature canes):
- *Shape*.—Medium thick.
- *Internode length*.—Medium, About 10.3 cm.
- *Width at node*.—About 1.0 cm.
- *Cross section*.—Circular to Elliptic.
- *Surface*.—Striate.
- *Main color*.—Can be any of the following colors; Yellowish brown; 166A and B and C, and 164A and B, and 176A and C.
- *Density of erect hairs of nodes*.—None or very sparse.
- *Density of erect hairs on internodes*.—None or very sparse.
- *Growth of axillary shoots*.—Strong; Approximately 34.8 cm.

Flowering shoot:
- *Vigor during flowering*.—Medium to Strong.
- *Attitude during flowering on shoots not tied*.—Erect to Semi-erect.
- *Color*.—Dorsal side of internodes — Green with Red stripes.
- *Color*.—Ventral side of internodes — Green.
- *Color*.—Dorsal side of nodes — Green with Red stripes.
- *Color*.—Ventral side of nodes — Green.
- *Density of prostrate hairs of nodes*.—None or Very sparse.
- *Density of erect hairs of nodes*.—None.
- *Density of prostrate hairs on internode*.—None.
- *Density of erect hairs on internode*.—None.
- *Anthocyanin coloration of buds*.—Absent.

Tendrils:
- *Distribution on the shoot* (*at full flowering*).—Discontinuous.
- *Length of tendril*.—Long; About 26.5 cm.
- *Thickness*.—Medium.
- *Color*.—Green; 145A.
- *Form*.—Bifurcated and Trifurcated.
- *Number of consecutive tendrils*.—2.

LEAVES

Young leaves:
- *Color of upper surface of first four distal unfolded leaves*.—Green with bronze spots.
- *Average intensity of anthocyanin coloration of fourth distal leaves prior to flowering*.—Medium.
- *Density of prostrate hairs between veins* (*lower surface*).—Absent.
- *Density of prostrate hairs on veins* (*lower surface*).—Very sparse.
- *Density of erect hairs between veins* (*lower surface*).—Absent.
- *Density of erect hairs on veins* (*lower surface*).—Very sparse.

Mature leaves:
- *Average length*.—About 16.2 cm.
- *Average width*.—About 19.7 cm.
- *Mature leaf size*.—Medium.
- *Shape of blade*.—Wedge-shaped.
- *Number of lobes*.—5.
- *Anthocyanin coloration of main veins on upper side of blade*.—Weak — Medium.
- *Mature leaf profile*.—V-shaped.
- *Blistering surface of blade upper surface*.—Weak.
- *Leaf blade tip*.—In the plane of the leaf.
- *Undulation of margin*.—Slight — Medium.
- *Thickness*.—Medium.
- *Undulation of blade between main and lateral veins*.—Absent.
- *Shape of teeth*.—Mixture of both sides straight and both sides convex.
- *Length of teeth*.—Medium.
- *Ratio length/width of teeth*.—Small.
- *Shape of upper lateral sinuses*.—Closed — Lobes slightly overlapping.
- *Depth of upper lateral sinuses*.—Medium.
- *Shape of base of upper leaf sinuses*.—V-shaped.
- *General shape petiole sinus*.—Lobes slightly overlapping.
- *Shape of base of petiole sinus*.—U shaped.
- *Tooth at petiole sinus*.—Absent.
- *Density of prostrate hairs between veins on lower surface of blade*.—Absent.
- *Density if erect hairs between veins on lower surface of blade*.—Absent.
- *Density of prostrate hairs on main veins on lower surface of blade*.—Very sparse.
- *Density of erect hairs on main veins on lower surface of blade*.—Sparse.
- *Density of prostrate hairs on main veins on upper surface of blade*.—Very sparse.
- *Density of erect hairs on main veins on upper surface of blade*.—None.
- *Autumn coloration of leaves*.—Leaves can be a single color or combination of colors, in a mottled pattern or on the edges of the leaves; Red-Purple; 59A, and 60A, and Yellow-Green; 152D and C, and 153B and C.

Upper surface:
*Color*.—Yellow-Green; 147A.
*Anthocyanin coloration of main veins*.—Weak — Medium.
*Surface appearance*.—Semi-glossy — Dull.
*Blistering surface of blade*.—Weak.
Lower surface:
*Color*.—Green; 146A.
*Glossiness*.—Weak.
*Surface texture*.—Smooth.
*Surface appearance*.—Dull.
Petiole:
*Length*.—About 12.8 cm.
*Length of petiole compared to middle vein*.—Slightly shorter.
*Density of prostrate hairs on petiole*.—None.
*Density of erect hairs on petiole*.—None.
Buds:
*Bud fruitfulness*.—Basal: Mostly fruitful.
*Position of first fruitful shoot on previous season cane*.—$1^{st}$ to 2nd node.
*Time of bud burst*.—Early, Mar. 3, 2010.

FLOWERS

General:
*Flower sex*.—Hermaphrodite.
*Length of first inflorescence*.—Long; about 23.0 cm long by 13.0 cm wide.
*Position of first flowering and fruiting node*.—$4^{th}$-$5^{th}$ node (current season growth).
*Number of inflorescence per flowering shoot*.—1.1 to 2.
*Time of bloom*.—Midseason as compared with similar varieties in the growing area of Delano, Calif.
*Date of full bloom*.—Mar. 18, 2010.

FRUIT

General:
*Ripening period*.—Medium; Approximately Aug. 23, 2010.
*Use*.—Fresh market.
*Keeping quality*.—Good.
*Resistance to*.—Insects: Average, typical of *Vitis vinifera* species; Diseases: Average, typical of *Vitis vinifera* species.
*Refractometer test*.—Solid-sugar: About 19.0 Brix.
*Brix/acid*.—About 38.8.
*Titratable acidity*.—About 0.49.
*Juice pH*.—About 3.82.
Cluster:
*Mature cluster length* (*peduncle excluded*).—About 29.6 cm.
*Mature cluster width*.—About 19.7 cm.
*Mature cluster weight*.—About 1422 g.
*Bunch density*.—Medium.
*Number of berries*.—About 139.
*Form*.—Circular to Cylindrical.
Peduncle:
*Lignification of peduncle*.—Medium.
*Length of peduncle*.—Approximately 6.3 cm.
Berry:
*Uniformity of size*.—Uniform.
*Single berry weight*.—About 12.8 g naturally; to about 14.9 g when treated with gibberellic acid or vine girdling.
*Shape*.—Ovate.
*Seeds*.—Seeded.
*Cross section*.—Circular.
*Berry dimensions*.—Longitudinal axis: About 33 mm. horizontal axis: About 25 mm.
*Berry firmness*.—Firm.
*Particular flavor*.—Neutral.
*Bloom* (*cuticular wax*).—Medium.
*Berry separation from pedicel*.—Difficult.
*Skin color* (*without bloom*).—Dark red-violet — blue-black; about 187A.
Skin:
*Thickness*.—Medium.
*Texture*.—Medium.
*Reticulation*.—Present.
*Tenacity*.—Tenacious to flesh.

What is claimed:

1. A new and distinct variety of grapevine as herein illustrated and described.

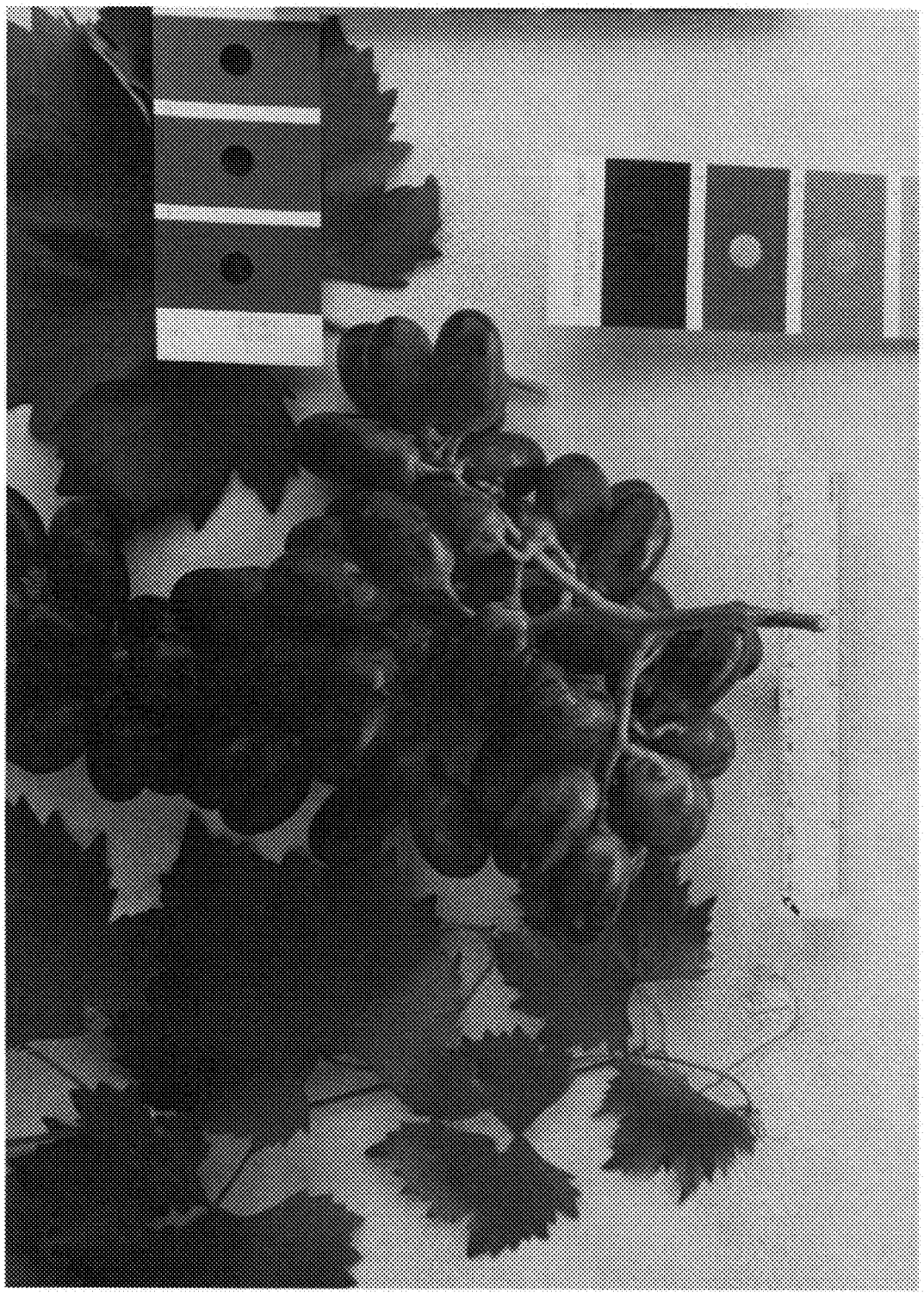

* * * * *